United States Patent
Vargas Fonseca

(10) Patent No.: US 11,253,161 B2
(45) Date of Patent: Feb. 22, 2022

(54) AUTOMATIC ZEROING SYSTEM AND ELECTRONIC LEVEL ADJUSTMENT OF PRESSURE TRANSDUCER APPLIED TO VITAL SIGNS MONITORS

(71) Applicant: ZAMMI INSTRUMENTAL LTDA, Rio de Janeiro (BR)

(72) Inventor: Luiz Henrique Vargas Fonseca, Rio de Janeiro (BR)

(73) Assignee: ZAMMI INSTRUMENTAL LTDA, Rio de Janeiro (BR)

( * ) Notice: Subject to any disclaimer, the term of this patent is extended or adjusted under 35 U.S.C. 154(b) by 549 days.

(21) Appl. No.: 16/338,109

(22) PCT Filed: Sep. 29, 2017

(86) PCT No.: PCT/BR2017/050293
§ 371 (c)(1),
(2) Date: Mar. 29, 2019

(87) PCT Pub. No.: WO2018/058227
PCT Pub. Date: Apr. 5, 2018

(65) Prior Publication Data
US 2020/0022596 A1    Jan. 23, 2020

(30) Foreign Application Priority Data

Sep. 29, 2016   (BR) .......................... 102016022714-3

(51) Int. Cl.
*A61B 5/0215*   (2006.01)
*A61B 5/00*   (2006.01)
(Continued)

(52) U.S. Cl.
CPC ........ *A61B 5/02156* (2013.01); *A61B 5/7203* (2013.01); *A61B 2560/0223* (2013.01);
(Continued)

(58) Field of Classification Search
CPC .......... A61B 2560/0223; A61B 5/0215; A61B 5/02156; A61B 5/7203; A61B 5/7225;
(Continued)

(56) References Cited

U.S. PATENT DOCUMENTS

| 5,668,320 A * | 9/1997 | Cowan | ..................... G01L 9/065 73/708 |
| 5,691,478 A * | 11/1997 | Barry | .................. A61B 5/02152 600/485 |
| 2016/0029904 A1* | 2/2016 | Quinn | .................. A61B 5/0024 600/499 |

FOREIGN PATENT DOCUMENTS

WO    WO-2009090646 A3 *   3/2010   ............. A61B 5/021

OTHER PUBLICATIONS

Kitchin, C. and Counts, L. Chapter VI: In-Amp and Diff Amp Applications Circuits. A Designer's Guide to Instrumentation Amplifiers. Analog Devices, 2004 (Year: 2004).*

* cited by examiner

*Primary Examiner* — David L Singer
*Assistant Examiner* — Anthony W Megna Fuentes
(74) *Attorney, Agent, or Firm* — Nath, Goldberg & Meyer; Jerald L. Meyer

(57) ABSTRACT

The present invention provides automatic zeroing and electronic level adjustment of pressure transducer in relation to patient, applied to vital signs monitors, where the automatic zeroing of circuit of pressure consists of circuit and software able to remove the value of the virtual ground voltage from the pressure calculation, and the electronic level adjustment of transducer in relation to patient consists of compensating, through software, the value in mmHg related to level difference in $cmH_2O$ informed by the user by means of monitor interface.

3 Claims, 2 Drawing Sheets

(51) Int. Cl.
  *A61M 25/00* (2006.01)
  *H03F 3/45* (2006.01)
  *G05F 5/00* (2006.01)
(52) U.S. Cl.
  CPC ............... *A61M 2025/0003* (2013.01); *A61M 2205/702* (2013.01)
(58) Field of Classification Search
  CPC ........ A61B 5/7475; A61M 2025/0003; A61M 2205/702; G05F 5/00; H03F 2200/261; H03F 2203/45138; H03F 3/45475
  See application file for complete search history.

AUTOMATIC ZEROING SYSTEM AND ELECTRONIC LEVEL ADJUSTMENT OF PRESSURE TRANSDUCER APPLIED TO VITAL SIGNS MONITORS

This is a National Phase Application filed under 35 U.S.C. 371 as a national stage of PCT/BR2017/050293, filed Sep. 29, 2017, claiming the benefit from Brazilian Application No. 1020160227143, filed Sep. 29, 2016, the content of each of which is hereby incorporated by reference in its entirety.

FIELD OF THE INVENTION

The present invention is related to an automatic zeroing system and electronic level adjustment of pressure transducer applied to vital signs monitors, deployed in hospitals or in other applications where patient monitoring is required.

BACKGROUND OF THE INVENTION

As is known to those skilled in the art, the monitoring of some vital signs is made invasively in order to check and control the hemodynamic condition of patients admitted either to Intensive Care Unit (ICU) or when they were undergone to high complexity surgeries. Such control includes, but is not limited to, continuous and real time monitoring of patient's intravascular pressures, being also possible the monitoring of internal pressure in heart chambers and principal veins and arteries, such as atriums, ventricles, pulmonary artery, vena cava, and aortic artery.

To deploy the monitoring of intravascular pressure in conventional fashion several components are required to compose the check and control system. FIG. 1 exemplify a conventional pressure monitoring scheme, in which the following is shown: serum support (1), the pressure bag (2), the disposable pressure transducer (3), the transducer support (4), the three-way stopcock (5), the pressure monitoring line (6) with saline solution attached to the patient's body through catheter (7), the interface cable (8) and the pressure monitor (9), being all of such components properly interconnected, working together as a blood pressure monitoring system.

The current monitors consist of a mainframe or console, where CPU, display and user interface are contained, still containing dedicated circuits related to each parameter to be monitored in addition to integrate the connectors and cables required for connection to the respective sensors.

As it is noted from the FIG. 1, in deployment of invasive pressure monitoring, it is essential the implantation of components that, due to its operation complexity, require the attendance of expert and trained professionals in order to occur no unforeseen event and to obtain a good monitoring.

Procedures required in deployment of patient invasive pressure monitoring include artery or vein puncture, and the suited catheter insertion, what should be done by a physician; circuit installation of pressure transducer, and the circuit "priming", its mounting in the support and connection to the monitor; monitor zeroing, and transducer leveling with patient's medium axillary line, what is usually done by nursing.

In monitor zeroing of the prior art, a circuit requiring pressure transducer zeroing before initiating the patient's monitoring is used. When the pressure transducer is zeroed, it is exposed to atmospheric pressure, and a command is triggered in the monitor to inform that the pressure being measured is the atmospheric pressure. This procedure is required since general pressure transducers are usually "Wheatstone" bridge type, as shown in FIG. 2. This circuit type provides in its output a differential voltage proportional to the pressure applied to the sensor; therefore, if a positive pressure is applied to the sensor, the voltage +Out will be higher than voltage −Out, where the inverse is also applied. For the other hand, when the applied pressure is zero, i.e., equal to atmospheric pressure, the voltages +Out and −Out are equal. Due to circuit configuration, usually composed by four equal resistances in bridge connection, the voltages +Out and −Out, in condition of zero pressure, are equal to the half of voltage (+In)−the voltage (−In), and, as usually, the voltage −In is connected to the ground, resulting in voltages +Out and −Out being equal to −In/2, in zero condition. For amplifying the signal of pressure sensor, which is very little, a differential type amplifier circuit is usually used, amplifying the difference between the voltages applied to its inputs; therefore depending of the pressure applied to sensor, the differential amplifier will show positive or negative voltages in its output.

The most of analogic to digital converters available in market, responsible for the conversion of analogical value of voltage in number to be processed by the microprocessor for calculating the pressure, only accepts positive voltage values, and, to solve this problem, the most of circuits used by those monitors uses a tool known as "virtual ground", changing the reference of ground circuit to a positive values, usually +Vcc/2, equal to voltage at pressure sensor output in condition of zero pressure; however, due to pressure sensor characteristics and components used in the circuit, it is difficult to exactly ensure what voltage is equivalent to "virtual ground".

With the aim of overcoming this problem, the zeroing system of pressure transducer was created according to the present invention. It is worth to emphasize that although the zeroing procedure of transducer is considered required and normal for the most users, in fact, it is a big inconvenient since in addition to being crucial its execution before initiating the monitoring, it should be repeated at least every 8 hours, due to the occurrence of a phenomenon known as "zero drift" or zero deviation, common to the most pressure sensors; moreover, this procedure should be only executed after the "warm-up time" of sensor, because if it is executed before that time, it has no utility due to the deviation occurring after the mentioned time interval.

The features of the prior art mentioned above represent big troubles to patients, else in urgency procedures, such as transportation procedures, because the pressure monitoring should be initiated as soon as possible in those situations, and every lost second of time is crucial for maintaining the patient safety. Other key factor is that the invasive and vascular access systems are increasingly become closed systems to avoid patient contamination due to exposure to environment air, however, during the zeroing, it is required to open the system and expose the transducer to atmospheric pressure, and it is usually executed by opening a three-way stopcock to environment air, therefore exposing the patient to contamination; in addition, the leaking of saline solution by the three-way stopcock connector is common, which may affect the pressure transducer connector, leading to its malfunctioning.

Other key concern related to the pressure monitoring is the transducer leveling against the patient medium axillary line, which is required because, since the circuit connecting the pressure transducer to catheter is full with saline solution, and since it is desired to measure the patient pressure against heart, if there is a level difference between the three-way stopcock of transducer and the patient heart, there will be pressure reading error equal to the level difference in units of cmH$_2$O and, insofar the pressure is measured in mmHg, for every positive centimeter of level difference, there will be an error of approximately 0.7 mmHg, obligating the transducer be mounted in the height of patient medium axillary line. This requirement imposes that the transducer is also leveled every time the patient change his/her position for avoiding reading errors.

Thus, in the light of previously mentioned major problems, the object of the present invention is to provide a zeroing system and electronic level adjustment of pressure transducer applied to vital signs monitor, aiming to overcome such problems, and also other consequent ones not mentioned herein.

SUMMARY DESCRIPTION OF THE INVENTION

The present invention consists of a circuit able to monitor a patient pressure, comprising the automatic zeroing and electronic level adjustment of pressure transducer in relation to patient, achieving the crucial features to best address its purposes.

BRIEF DESCRIPTION OF THE DRAWINGS

Automatic zeroing system and electronic level adjustment of pressure transducer in relation to patient, according to the present invention, will be best understood from the attached illustrative figures, which represents in a schematic and non-limitative way of its scope.

DETAILED DESCRIPTION OF THE INVENTION

Figure 1:
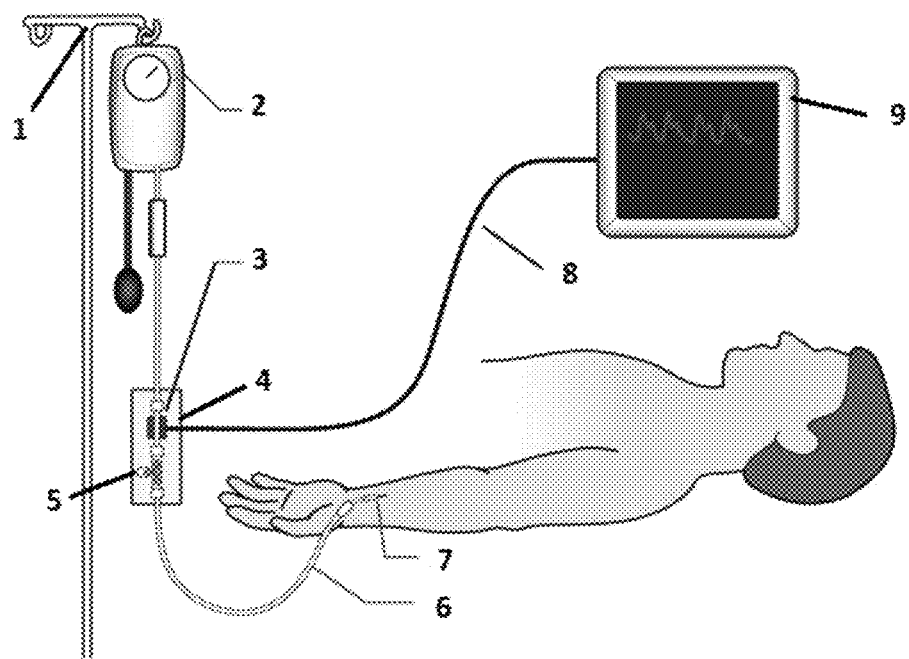
FIG. 1—Typical invasive pressure monitoring system of the prior art.
Figure 2:
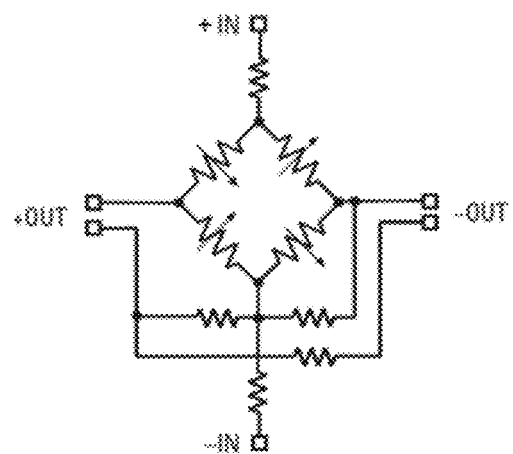
FIG. 2—Scheme of a pressure transducer circuit of "Wheatstone" bridge type of the prior art.

FIGS. 1 and 2 regarding the monitor and "wheatstone" bridge type circuit of the prior art were already described above for reference.

Thus, the present invention provides the automatic zeroing and electronic level adjustment of pressure transducer in relation to patient, in order to provide the assemble with no requirement of running the pressure sensor zeroing, either in initiation as well as every 8 hours, and to connect the pressure transducer to the monitor and initiating the pressure monitoring is the only requirement.

Figure 3:
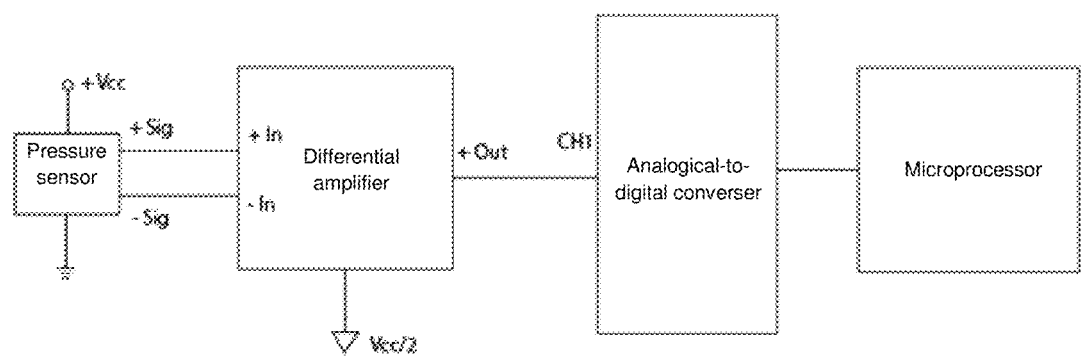
FIG. 3—Block diagram featuring a traditional pressure measurement circuit.

In block diagram of FIG. 3, it is shown a traditional pressure measurement circuit, in which an floating reference is part of calculation of pressure value; i.e., assuming the use of analogic to digital converter of 10 bits, this will indicate values between 0 and 1023 in its output, representing voltages between 0 and Vref, and assuming Vref is equal to +Vcc, which in turn is equal to +5 V, having the virtual ground at 2.5 V, and, for such voltage value, the analogic to digital converter will indicate the value 512 in its output. When the zeroing is executed, the microprocessor is informed that the value 512 is corresponding to zero pressure, and, therefore, values above 512 are considered positive, and values below 512 are considered negative; i.e., the voltage at the output of differential amplifier is equal to:

$$+\text{Out}=(((+Sig)-(-Sig))\times\text{gain})+Vcc/2$$

where:
+Out—output voltage of differential amplifier;
+Sig—positive output voltage of pressure sensor;
−Sig—negative output voltage of pressure sensor;
Gain—voltage gain of differential amplifier;
+Vcc/2—half of power supply voltage of pressure sensor and of amplifier.

If value of +Vcc/2 fluctuate, the output voltage will also fluctuate, even if the pressure is the same, and, therefore, the zeroing every 8 hours is required, and constitutes the trouble of pressure monitors of the prior art.

Figure 4:
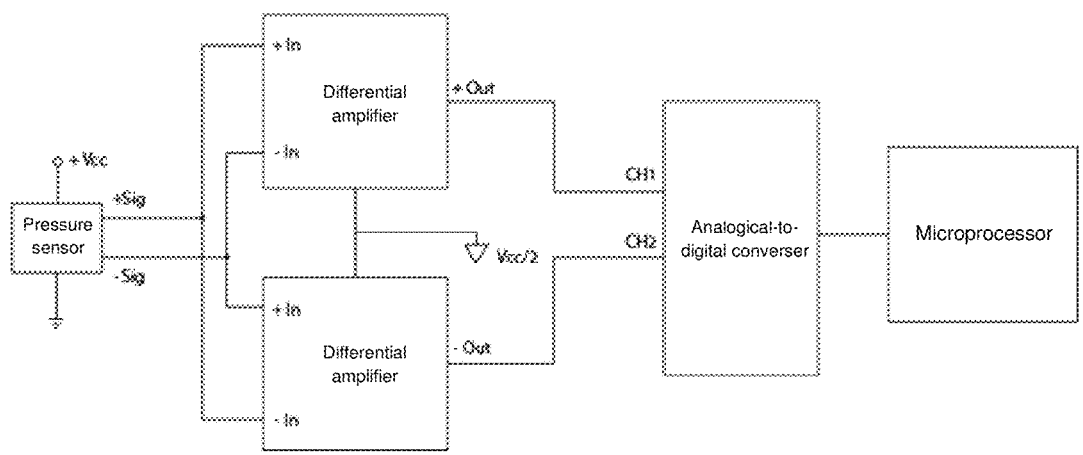
FIG. 4—Block diagram featuring pressure measurement circuit according to the present invention.

In automatic zeroing provided by the present invention, the solution for avoiding the reference fluctuating trouble (+Vcc/2) consists of removing the reference from the pressure calculation, what should be done with circuit of FIG. 4, in conjunction with specific software, using two differential amplifiers, with inverted inputs to each other to amplify the signal, else adding the virtual ground (+Vcc/2), and where the first differential amplifier provides voltage higher than +Vcc/2 for positive pressures, while the second differential amplifier provides voltage higher than +Vcc/2 for negative pressures, and, at condition of zero pressure, both differential amplifiers provide voltage equal to +Vcc/2, having the following equations for output voltages from two amplifiers:

$$\text{Out1}=((+Sig)-(-Sig))\times\text{gain}+Vcc/2$$

$$\text{Out2}=((-Sig)-(+Sig))\times\text{gain}+Vcc/2$$

where:
Out1—output voltage of differential amplifier 1;
Out2—output voltage of differential amplifier 2;
+Sig—positive output voltage of pressure sensor;
−Sig—negative output voltage of pressure sensor;
Gain—voltage gain of differential amplifier;
+Vcc/2—half of power voltage of pressure sensor and of amplifier.

Applying these voltages to analogic to digital converter inputs, the following values are achieved:

$$\text{Value}CH1=\text{value}(((+Sig)-(-Sig))\times\text{gain})+\text{value}(Vcc/2)$$

$$\text{Value}CH2=\text{value}(((-Sig)-(+Sig))\times\text{gain})+\text{value}(Vcc/2)$$

where:
ValueCH1—number value achieved by analogic to digital converter corresponding to output signal of differential amplifier 1(Out1);
ValueCH2—number value achieved by analogic to digital converter corresponding to output signal of differential amplifier 2(Out2);
value(((+Sig)−(−Sig))×gain)—number value achieved by analogic to digital converter corresponding to output voltage of differential amplifier 1 without virtual ground;
value(((−Sig)−(+Sig))×gain)—number value achieved by analogic to digital converter corresponding to output voltage of amplifier 2 without virtual ground.
value (Vcc/2)—number value achieved by analogic to digital converter corresponding to virtual ground, in which the optimal conditions would be 512.

As can be seen from the block diagram of FIG. 4 and from the above equations, the value related to voltage of virtual ground is present in values of ValueCH1 and ValueCH2, therefore, when it is subtracted one from another, the value of Vcc/2 is eliminated, not impacting in final pressure value, as can be noted from the following equation:

$$\text{Pressure}=(\text{Value}CH1-\text{Value}CH2)\times\text{Scaleadjustment}$$

where:
Pressure—final pressure value calculated in mmHg;
ValueCH1—number value achieved by analogic to digital converter corresponding to output signal of differential amplifier 1(Out1);
ValueCH2—number value achieved by analogic to digital converter; corresponding to output signal of differential amplifier 2(Out2);
Scaleadjustment—conversion factor of value achieved by analogic to digital converter for value in mmHg.

Therefore, using software suitable for calculating the equations above, a circuit able to measure pressures both positive and negative can be achieved, without requiring to run the zeroing, which results in great advantages, such as, e.g., the prompt start of monitoring, just by connecting the pressure transducer to monitor for initiating it, dispensing the requirement of waiting the "warm-up time", for measurements effect, disregarding the voltage fluctuations of virtual ground; the no requirement for opening the system to expose the transducer to atmospheric pressure which eliminates the contamination risk and damage to electrical connections due to serum leakage during the zeroing; circuit immune from noises due to the fact that both amplification as well as pressure calculation are performed in a differential way.

The electronic level adjustment of transducer in relation to patient may be performed by deploying the following equation in software:

$$Pressure=(ValueCH1-ValueCH2)\times Scaleadjustment+Leveladjustment$$

where:
Pressure—final pressure value calculated in mmHg;
ValueCH1—number value achieved by analogic to digital converter corresponding to output signal of differential amplifier 1 (Out1);
ValueCH2—number value achieved by analogic to digital converter corresponding to output signal of differential amplifier 2(Out2);
Scaleadjustment—conversion factor of value achieved by analogic to digital converter for the value in mmHg;
Leveladjustment—value in mmHg, corresponding to level difference in cmH$_2$O between patient and pressure transducer, informed by the user through a monitor interface.

This value is positive when the transducer is higher than patient, and negative when the transducer is lower than patient, and the level difference value should be measured by the user and informed to the monitor through its interface, and, therefore, the transducer may be positioned anywhere, with no requirement that it stays in support close to patient; further, if patient change from position, or in case of transportation, it is enough to inform the height difference between transducer and patient at the monitor, and the level difference will be automatically corrected. Other observed advantage is the possibility for measuring the patient pressure against other points of body, besides the heart.

The skilled in the art will understand that the features shown herein are not limited to monitoring of parameters disclosed herein as example, but also to other ones no mentioned herein.

The invention claimed is:

1. Automatic zeroing system and electronic level adjustment of pressure transducer applied to vital signs monitors, comprising circuit and software working together to remove the value of virtual ground voltage from a pressure calculation, and electronically adjusting the level of the pressure transducer in relation to a patient, through software for value compensation in mmHg related to level difference in cmH$_2$O informed by a user by means of monitor interface through the software;

wherein said automatic zeroing system uses two differential amplifiers with inputs inverted to each other adding to said inputs the virtual ground; and wherein said automatic zeroing and the electronic adjustment at the level at the pressure transducer with respect to the patient are simultaneously performed according to the equation:

$$Pressure=(ValueCH1-ValueCH2)\times scaleAdjustment+levelAdjustment$$

where:
Pressure—final pressure value calculated in mmHg;
ValueCH1—number value achieved by an analog-to-digital converter corresponding to an output signal of a first differential amplifier;
ValueCH2—number value achieved by the analog-to-digital converter corresponding to an output signal of a second differential amplifier;
scaleAdjustment—conversion factor achieved by the analog-to-digital converter in mmHg;
levelAdjustment—value in mmHg, corresponding to level difference in cmH$_2$O between the patient and the pressure transducer, informed by the user through the monitor interface.

2. The system according to claim 1, wherein said first differential amplifier provides voltages higher than the virtual ground voltage for positive pressures and said second amplifier provides voltages higher than the virtual ground voltage for negative pressures, and, in condition of zero pressure, both differential amplifiers provide a voltage equal to the virtual ground voltage.

3. The system according to claim 2, wherein said voltages are applied to inputs of two different channels of the analog-to-digital converter.

* * * * *